United States Patent [19]

Büschken et al.

[11] Patent Number: 5,416,215
[45] Date of Patent: May 16, 1995

[54] PROCESS TO PREPARING 2,2,6,6-TETRA-METHYLPIPERIDINE-N-OXYL AND ITS 4-POSITION SUBSTITUTED DERIVATIVES

[75] Inventors: Wilfried Büschken, Haltern; Manfred Kaufhold, Marl; Peter Bickert, Münster, all of Germany

[73] Assignee: Huels Aktiengesellschaft, Marl, Germany

[21] Appl. No.: 73,472

[22] Filed: Jun. 9, 1993

[30] Foreign Application Priority Data

Jun. 13, 1992 [DE] Germany .................. 42 19 459.8

[51] Int. Cl.$^6$ .................................. C07C 211/38
[52] U.S. Cl. .................................. 546/184; 546/242
[58] Field of Search .................................. 546/242, 184

[56] References Cited

FOREIGN PATENT DOCUMENTS

| | | |
|---|---|---|
| 0157738 | 10/1985 | European Pat. Off. . |
| 0233622 | 8/1987 | European Pat. Off. . |
| 0488403 | 6/1992 | European Pat. Off. . |
| 983134 | 2/1965 | United Kingdom . |
| 2048842 | 12/1980 | United Kingdom . |

OTHER PUBLICATIONS

Synthesis, Nov. 11, 1987, pp. 1015–1017, P. Brougham, et al., "Oxidation Reactions Using Magnesium Monoperphthalate . . . "
Soviet Patents Abstracts, Jul. 31, 1991, Derwent Publications Ltd., AN-91-176790, SU-A-1 583 415, Aug. 7, 1990.

Primary Examiner—Howard T. Mars
Assistant Examiner—John Peabody
Attorney, Agent, or Firm—Oblon, Spivak, McClelland, Maier, & Neustadt

[57] ABSTRACT

A process is described for preparing 2,2,6,6-tetramethylpiperidine-N-oxyl and its 4-position substituted derivatives by oxidation of 2,2,6,6-tetramethylpiperidine and its 4-position substituted derivatives in the presence of hydrogen peroxide and low concentrations of divalent metal salts.

20 Claims, No Drawings

PROCESS TO PREPARING 2,2,6,6-TETRA-METHYLPIPERIDINE-N-OXYL AND ITS 4-POSITION SUBSTITUTED DERIVATIVES

BACKGROUND OF THE INVENTION

1. Field of the Invention

The present invention relates to a process for preparing 2,2,6,6-tetramethylpiperidine-N-oxyl (TEMP-N-oxyl) and its 4-position substituted derivatives by oxidizing 2,2,6,6-tetramethylpiperidine (TEMP) or its 4-position substituted derivatives with hydrogen peroxide in the presence of low concentrations of water-soluble light or heavy divalent metal salts:

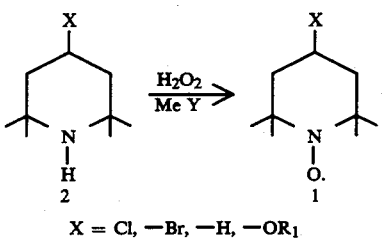

$X = Cl, -Br, -H, -OR_1$ wherein formula 2 above is TEMP and formula 1 above is TEMP-N-oxyl and $R_1$ is hydrogen, a linear or branched $C_1-C_{20}$ alkyl group (particularly methyl, ethyl, n-and i-propyl and n- and tert-butyl), benzyl,

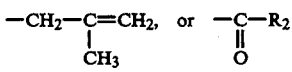

and $R_2$ is hydrogen, a linear or branched $C_1-C_{20}$ alkyl group or phenyl, and MeY is the divalent metal salt.

2. Description of the Prior Art

The synthesis of N-oxyls by oxidation of tertiary amines is known in the literature and differ from the present invention primarily with respect to the oxidizing agent used. For Example, R. Winter and R. Malherbe conduct the oxidation of N-oxyls with organic hydroperoxides, e.g., tert-butyl hydroperoxide (see EP-A 0 157 738), thus using an expensive oxidizing agent which produces a coupling byproduct in at least stoichiometric quantities. This byproduct also exists when percarboxylic acids are used as oxidizing agents. Chou et al use, for example, 3-chloroperoxide benzoic acid as an oxidizing agent (see J. Org. Chem. 39 [1947] 2356, 2360).

A much better oxidizing agent than organic hydroperoxides and percarboxylic acids is hydrogen peroxide because it is inexpensive and because water is produced as the coupling byproduct. D. P. Young et al use hydrogen peroxide as an oxidizing agent in the presence of a salt of tungstic acid as catalyst (see GB-P 1 199 351 and Tetrahedron 20 [1964] 131, 137). The drawbacks of this process, however, are the extremely long reaction times (on the order of several days) and the problem that arises when disposing of the catalyst, since it may not be flushed away with the waste water for reasons relating to environmental regulations, etc. Even when sodium carbonate is used, long reaction times result (see Soviet Physics Doklady 261, 1, 103–110, [1981]).

Tungstophosphoric acid has been used to reduce the reaction time of oxidation, but again the problems relating to disposal of the catalyst and its expense remain (see Cf. R. Briére, H. Lemaire and A. Rassat, Bull. Soc. Chim. France, 11, 3273 [1965]).

In addition to these problems, all the above-described oxidation methods have a high rate of consumption of chemical oxidizing agents and catalysts, and employ complicated procedures, while some are very time-consuming.

OBJECTS OF THE INVENTION

An object of the present invention is to develop a process wherein TEMP and its 4-position substituted derivatives can be oxidized with hydrogen peroxide quickly without having to dispose of an environmentally damaging catalyst. There is great interest in such a process because the N-oxyl of TEMP and its 4-position substituted derivatives are important stabilizers for polymeric materials and are particularly useful as light stabilizers. In addition, these N-oxyls have gained importance as redox catalysts, are precursors for other N-oxyl derivatives and are useful as ESR spin probes.

Another object of the present invention is to develop a process for the preparation of 2,2,6,6-tetramethylpiperidine-N-oxyl and its 4-position substituted derivatives of formula 1 through oxidation of 2,2,6,6-tetramethylpiperidine and its 4-position substituted derivatives of formula 2 by means of hydrogen peroxide:

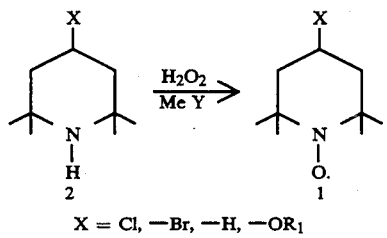

$X = Cl, -Br, -H, -OR_1$ wherein the oxidation is catalyzed by low concentrations of divalent metal salts (MeY) where $R_1$ is hydrogen, a linear or branched $C_1-C_{20}$ alkyl group, benzyl,

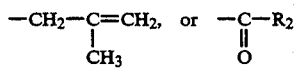

and $R_2$ is hydrogen, a linear or branched $C_1-C_{20}$ alkyl group or phenyl.

DETAILED DESCRIPTION OF THE INVENTION

According to the present invention, TEMP and its 4-position substituted derivatives are oxidized virtually quantitatively with very high selectivity (exceeding 90%, in some cases exceeding 97%), by hydrogen peroxide in the presence of low concentrations of divalent metal salts. Salts of magnesium, calcium, other alkaline earth metals such as barium and strontium and salts of zinc can be added as the divalent metal salts, e.g., in the form of chlorides, sulfates, nitrates, phosphates, hydroxides, etc. The salts must be water-soluble and present as ions in the reaction mixture. Metal $C_1-C_5$ linear or branched alcoholates or Grignard compounds or the metals themselves can also be used and are included in the term "salts". The salts can be added as pure material or in solution and may also be used as mixtures.

The metal salts are used in extremely low concentrations and provide good overall yields of oxidized product. The molar ratio of TEMP to the metal salt ranges from $10^5:1$ to $10:1$, preferably $10^5:1$ to $10^2:1$, more preferably $10^4:1$. Catalyst consumption is very low in the invention process, and the metal salts are extremely inexpensive chemicals. Another advantage of the invention is that the catalysts utilized are chemicals that do not pollute the environment, since compounds of, e.g., magnesium and calcium are wide-spread in nature; traces of these compounds in the waste products of the invention process do not result in environmental protection problems.

The conversion of TEMP to TEMP-N-oxyl (and its 4-position substituted derivatives) according to the present invention is effected in aqueous solution or in suspension. Whether an organic solvent is added depends upon the polarity or the solubility of the compound to be oxidized in water. If, for example, 4-hydroxy-TEMP ($x=OR_1$, $R_1=H$), a very polar material, is used as the reactant then no further solvent is necessary.

Conversely a solvent that solubilizes TEMP is added in the case of the very nonpolar TEMP molecules including TEMP itself ($x=H$). For economic reasons, simple, low boiling alcohols or diols such as methanol, ethanol, n- or iso-propanol, tert-, iso- or n-butanols, ethylene glycol, propylene glycol, ethylene diglycol, propylene diglycol, etc., alkyl glycol ether, dioxan-1,4 or -1,3, tetrahydrofuran and similar compounds are used as the solvent. Preferred solvents are methanol, ethanol and iso-propanol. Instead of a pure solvent, mixtures of two or more solvents can also be added.

The amount by weight of solvent ranges from 1 to 10 times, preferably 2 to 1.1 times the amount by weight of TEMP or TEMP derivative. The optimal amount for the respective compound to be added can, if desired, be determined in a pilot test. The more polarizable the compound is, the smaller the amount of solvent necessary; TEMP and 4-hydroxy-TEMP may be regarded as two extremes between which all other derivatives lie. Hydrogen peroxide can be added in its commercially available forms as a 10 to 90% aqueous solution.

A typical oxidation reaction according to the present invention includes providing a reaction mixture of TEMP or a TEMP derivative, one or more invention metal salt catalysts and water (where the amount by weight of water corresponds to 0.1 to 2 times, preferably 0.3 to 0.8 times the amount by weight of TEMP or TEMP derivative). The temperature of the reaction mixture is adjusted to from 0° to 100° C. preferably to from 40° to 90° C. Within 0.1 to 2 hours the hydrogen peroxide is added dropwise and the mixture is stirred for another 1 to 30, preferably 5 to 15 hours, at the chosen temperature. The molar ratio of TEMP or TEMP derivative to hydrogen peroxide ranges from 1:1 to 1:10, preferably from 1:1 to 1:5, in particular 1:1.5 to 1:2.5. It is especially advantageous to add $H_2O_2$ in 105 to 135% of the stoichiometric amount.

The reaction sequence is monitored by means of gas chromatographic analysis and work-up is carried out according to typical methods known in the art. Since the starting compound is almost totally converted workup is quite simple. For example, during the oxidation of 4-hydroxy-TEMP, during which process no solvent is required, the work-up is accomplished by simply removing water by distillation under vacuum. The corresponding N-oxyl has a purity of more than 99% and remains as the residue. Since the catalyst concentration in the end product is less than 100 ppm, separation is superfluous for most applications. Of course, the reaction product can be purified by recrystallization, etc. and at the same time the catalyst can be removed.

Having generally described this invention, a further understanding can be obtained by reference to certain specific examples which are provided herein for purposes of illustration only and are not intended to be limiting unless otherwise specified.

EXAMPLE 1

Oxidation of 4-hydroxy-TEMP

Using a glass apparatus comprising a three neck flask equipped with a stirrer, thermometer and dropping funnel,

| | |
|---|---|
| 314 g (2.0 mole) | 4-hydroxy-TEMP |
| 250 ml | water |
| 11.6 mg (0.2 mmole) | magnesium hydroxide |
| 453 g (4.0 mole) | hydrogen peroxide (30%) | are provided and a suspension is produced by adding 4-hydroxy-TEMP to the water. The magnesium hydroxide is added and the mixture heated to 70° C.

At this temperature the 30% aqueous $H_2O_2$ solution is added drop by drop over 2 hours. The mixture is stirred for another 10 hours at 70° C. When the mixture reaches 90° C. and a pressure of 4 hPa the water is withdrawn. The residue (340 g) solidifies while cooling to room temperature. The 4-hydroxy-TEMP-N-oxyl content is 99.8%, corresponding to a yield of 98.6%. The melting point ranges from 71° to 72° C.

EXAMPLE 2

Oxidation of 4-hydroxy-TEMP

The apparatus described in example 1 was used, as were the amounts of 4-hydroxy-TEMP and water specified there. As the catalyst 40.6 mg (=0.2 mmole) magnesium chloride hexahydrate: $MgCl_2 \cdot 6H_2O$ was added. Then at 70° C. 453 g (4 mole) 30% aqueous $H_2O_2$ solution was added dropwise over 2 hours. The mixture was stirred for 15 hours at 70° C. After withdrawing the water, 342 g of residue with a 4-hydroxy-TEMP-N-oxyl content of 99.3% remains, corresponding to a yield of 98.7%. The melting point ranges from 71° to 72° C.

EXAMPLE 3

Oxidation of 4-hydroxy-TEMP

Using the apparatus described in example 1, 4-hydroxy-TEMP and water in amounts specified in Example 1 were provided and the catalyst 114 mg (0.5 mmole) magnesium sulfate hexahydrate $MgSO_4 \cdot 6H_2O$ was added. Then at 70° C. 453 g (4 mole) 30% aqueous $H_2O_2$ solution was added dropwise over 2 hours. The mixture was stirred for 15 hours at 70° C. After withdrawing the water, 340 g of residue with a 4-hydroxy-TEMP-N-oxyl content of 99.2% remains, corresponding to a yield of 98%. The melting point ranges from 71° to 72° C.

EXAMPLE 4

Oxidation of TEMP

Using the apparatus described in example 1, and installing a reflux condenser:

| | |
|---|---|
| 28.25 g (0.2 mole) | TEMP |
| 46 ml | methanol |
| 4.07 mg (=0.02 mmole) | magnesium chloride hexahydrate, $MgCl_2 \cdot 6H_2O$, dissolved in 1 ml of water. | were provided. TEMP, methanol and the magnesium chloride solution were combined and heated to 65° C. Then, over 45 minutes 45.3 g (0.4 mole) 30% aqueous $H_2O_2$ solution was added dropwise and stirred for 7 hours at 65° C. Gas chromatographic analysis showed:

| | |
|---|---|
| TEMP content | 4.4% |
| TEMP-N-oxyl content | 92.5% |

Thus, the conversion exceeded 95%.

To purify the N-oxyl, 5 ml of 10% sulfuric acid was added and the reaction mixture was extracted four times with 50 ml of cyclohexane. The cyclohexane was removed by distillation, and 27.1 g of TEMP-N-oxyl are obtained as dark red crystals with a purity of 98.7%. The yield is 85.5.

EXAMPLES 5 TO 11

Using the apparatus described in example 1, the reagents specified in example 4 were reacted with the difference that, instead of TEMP, the TEMP derivatives listed in the following table were used. Oxidation and work-up are as described in example 4. The results shown in the table below.

The following reagents were used:

| Temp Derivative | Chemical Formula |
|---|---|
| 5. acetate | formula 2, $x = OR_1$, $R_1 = -\overset{O}{\underset{\|}{C}}-R_2$, $R_2 = -CH_3$ |
| 6. benzoate | formula 2, $x = OR_1$, $R_1 = -\overset{O}{\underset{\|}{C}}-R_2$, $R_2 = -C_6H_5$ |
| 7. pivaloate | formula 2, $x = OR_1$, $R_1 = -\overset{O}{\underset{\|}{C}}-R_2$, $R_2 = -\overset{CH_3}{\underset{CH_3}{\overset{\|}{C}}}-CH_3$ |
| 8. chlorine derivative | formula 2, x = Cl |
| 9. methyl ether | formula 2, $x = OR_1$, $R_1 = -CH_3$ |
| 10. benzyl ether | formula 2, $x = OR_1$ $R_1 = -CH_2-C_6H_5$ |
| 11. octyl ether | formula 2, $x = OR_1$ $R_1 = -C_8H_{17}$ |

The final products of Examples 5 to 11 have a structure according to formula 1 above, wherein the meaning of x, $R_1$ and $R_2$ remain unchanged with respect to the TEMP derivative reagent used.

| Reagent | Final Product | | | |
|---|---|---|---|---|
| TEMP Derivative | Purity % | Melting Point °C. | Conversion in % | Yield in % |
| 1. acetate | 98.0 | 71 | 97.0 | 90 |
| 2. benzoate | 97.3 | 112 to 114 | 93.2 | 88 |
| 3. pivaloate | 98.2 | 106 to 108 | 96.5 | 91 |
| 4. chlorine | 99.0 | | 98.0 | 85 |

-continued

| Reagent | Final Product | | | |
|---|---|---|---|---|
| TEMP Derivative | Purity % | Melting Point °C. | Conversion in % | Yield in % |
| derivative | | | | |
| 5. methyl ether | 99.2 | 69 to 72 | 99.1 | 84 |
| 6. benzyl ether | 97.5 | | 95.8 | 82 |
| 7. octyl ether | 97.3 | | 97.1 | 81 |

What is claimed as new and desired to be secured by Letters Patent of the United States is:

1. A process for preparing 2,2,6,6-tetramethylpiperidine-N-oxyl and its 4-position substituted derivatives of formula 1 through oxidation of 2,2,6,6-tetramethylpiperidine and its 4-position substituted derivatives of formula 2 in the presence of hydrogen peroxide and at least one divalent metal salt,

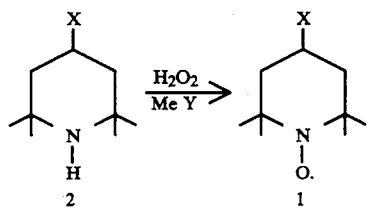

where X is Cl, Br, H or $OR_1$, where $R_1$ is hydrogen, a linear or branched $C_1$–$C_{20}$ alkyl group, benzyl,

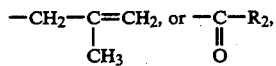

$R_2$ is hydrogen, a linear or branched $C_1$–$C_{20}$ alkyl group or phenyl, and MeY is the divalent metal salt, wherein said at least one divalent metal salt comprises a salt of an alkaline earth metal, a salt of zinc or a mixture thereof.

2. A process as claimed in claim 1, wherein the at least one divalent metal salt comprises a salt of an alkaline earth metal.

3. A process as claimed in claim 1, wherein the at least one divalent metal salt is a chloride, sulfate, nitrate, phosphate or hydroxide.

4. A process as claimed in claim 1, wherein the at least one divalent metal salt is a magnesium salt.

5. A process as claimed in claim 1, wherein the molar ratio of 2,2,6,6-tetramethylpiperidine or its 4-position substituted derivatives to the at least one metal salt ranges from $10^5$:1 to $10^2$:1.

6. A process as claimed in claim 1, wherein the oxidation takes place in homogeneous aqueous solution or in aqueous suspension.

7. A process as claimed in claim 1, wherein the oxidation takes place in a mixture of water and an organic solvent.

8. A process as claimed in claim 7, wherein the organic solvent is selected from the group consisting of methanol, ethanol, n- or iso-propanol, tert-, iso- or n-butanol, ethylene glycol, propylene glycol, ethylene diglycol, propylene diglycol, alkyl glycol ether 1,3-dioxan, 1,4-dioxan, tetrahydrofuran and mixtures thereof.

9. A process as claimed in claim 1, wherein said hydrogen peroxide is added as a concentrate in water, having a concentration range of from 10 to 90% by volume.

10. A process as claimed in claim 1, wherein said hydrogen peroxide is present in 105% to 135% of the stoichiometric amount.

11. A process as claimed in claim 1, wherein the oxidation is effected at a temperature ranging from 0° to 100° C.

12. A process as claimed in claim 4, wherein said magnesium salt is selected from the group consisting of $Mg(OH)_2$, $MgSO_4 \cdot 6H_2O$, $MgCl_2 \cdot 6H_2O$, $Mg(NO_3)_2$ and mixtures thereof.

13. A process as claimed in claim 5, wherein said molar ratio is $10^4:1$.

14. A process as claimed in claim 7, wherein the organic solvent is an alcohol or a diol.

15. A process as claimed in claim 7, wherein the organic solvent comprises methoxyethanol or ethoxyethanol.

16. A process as claimed in claim 9 wherein said concentration range is from 30 to 40% by volume.

17. A process as claimed in claim 11 wherein said temperature is from 40° to 90° C.

18. A process as claimed in claim 1, wherein said at least one divalent metal salt consists of a salt of an alkaline earth metal.

19. A process as claimed in claim 1, wherein said at least one divalent metal salt consists of a salt of zinc.

20. A process as claimed in claim 1, wherein said at least one divalent metal salt consists of a mixture of an alkaline earth metal and a salt of zinc.

* * * * *